United States Patent [19]
Ameil et al.

[11] Patent Number: 6,086,588
[45] Date of Patent: Jul. 11, 2000

[54] OSTEOSYNTHESIS SYSTEM FOR VERTEBRA ARTHRODESIS

[75] Inventors: Marc Ameil, Reims; Jean Huppert, L'Etrat; Jean-Louis Jermann, Chaumont; Thierry Marnay, Montpellier, all of France

[73] Assignee: Aesculap AG & Co. KG, Tuttlingen, Germany

[21] Appl. No.: 09/202,437

[22] PCT Filed: May 5, 1998

[86] PCT No.: PCT/FR98/00897

§ 371 Date: Jul. 16, 1999

§ 102(e) Date: Jul. 16, 1999

[87] PCT Pub. No.: WO98/49960

PCT Pub. Date: Nov. 12, 1998

[30] Foreign Application Priority Data

May 7, 1997 [FR] France .................................. 97 05641

[51] Int. Cl.⁷ .................................................. A61B 17/70
[52] U.S. Cl. .................................................. 606/61; 606/73
[58] Field of Search .................................. 606/61, 69, 72, 606/73

[56] References Cited

U.S. PATENT DOCUMENTS

| | | | |
|---|---|---|---|
| 5,403,314 | 4/1995 | Currier | 606/61 |
| 5,735,851 | 4/1998 | Errico et al. | 606/61 |
| 5,741,255 | 4/1998 | Krag et al. | 606/61 |
| 5,743,907 | 4/1998 | Asher et al. | 606/61 |
| 5,776,135 | 7/1998 | Errico et al. | 606/61 |
| 5,810,819 | 9/1998 | Errico et al. | 606/61 |

Primary Examiner—Michael Buiz
Assistant Examiner—David O. Reip
Attorney, Agent, or Firm—Harrison & Egbert

[57] ABSTRACT

An osteosynthesis system for vertebral arthrodesis, having at least one vertebral compression or distraction bar capable of extending over a portion at least of the rachis; at least one vertebral anchoring member having an end head with a spherical surface, an intermediate shank and a vertebral anchoring portion; and, associated with each anchoring member, a common support for receiving, coupling and immobilizing the vertebral anchoring member and the bar, the common support including a first concave housing for receiving the bar, a second concave housing, for receiving the spherical head, and a screwthreaded member, for immobilization of the bar and the anchoring member on the support, the immobilization member having at least one nut which is screwed onto a screwthreaded portion of the support. The first housing is disposed to the exterior of the screwthreaded portion of the support and is open laterally and upwardly, in opposite relationship to the rachis, so that the bar is immobilized by a peripheral portion of the nut.

22 Claims, 3 Drawing Sheets

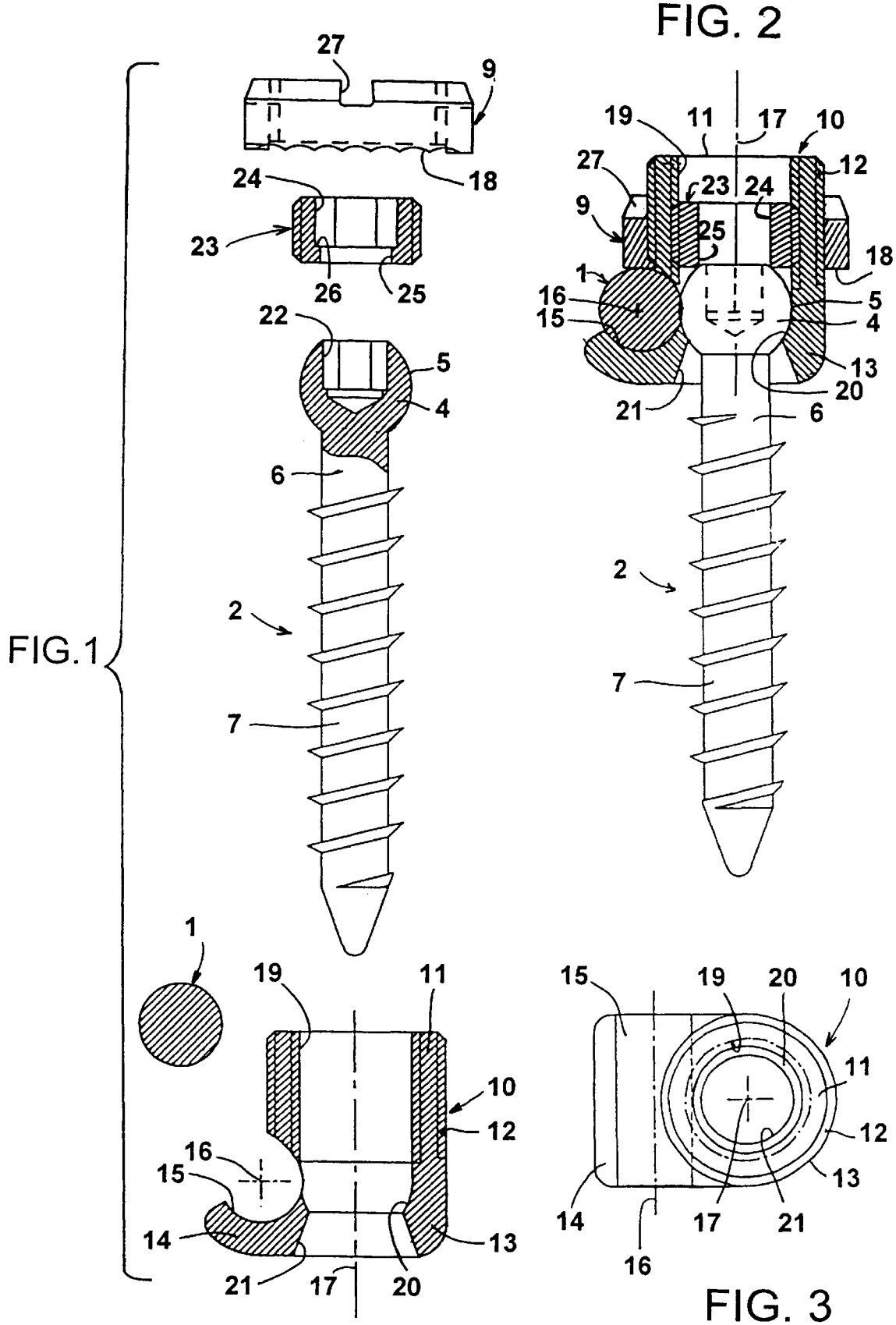

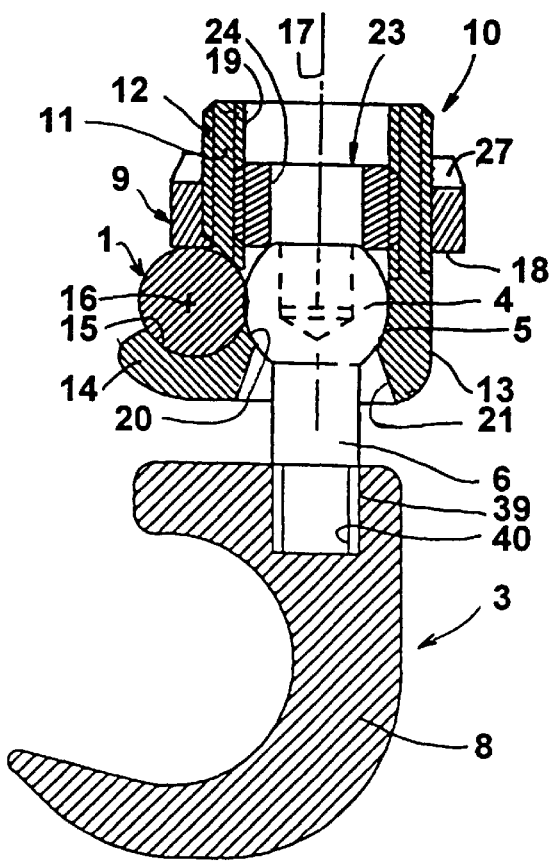
FIG. 4
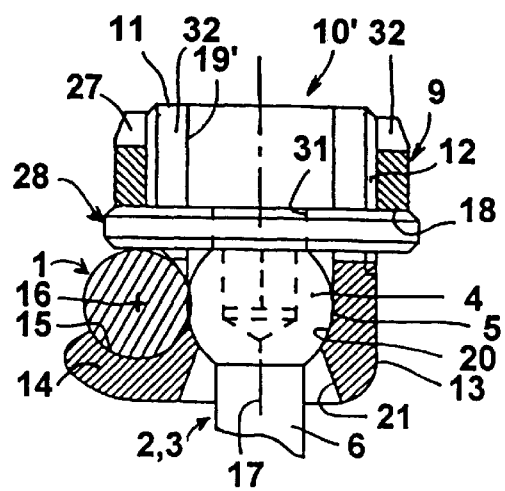
FIG. 5
FIG. 6
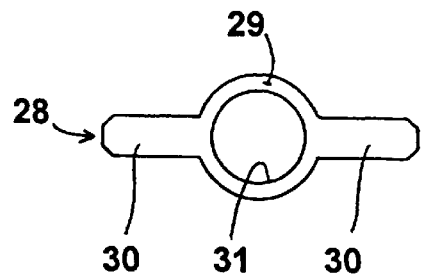
FIG. 7

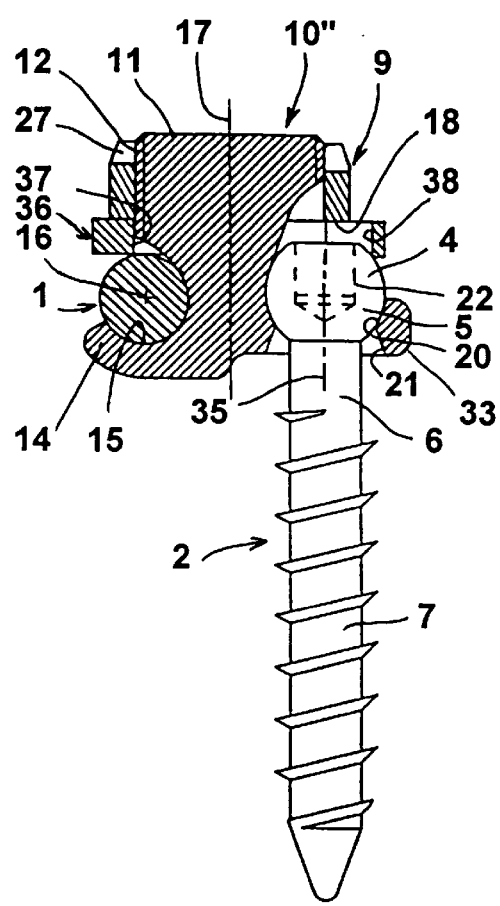
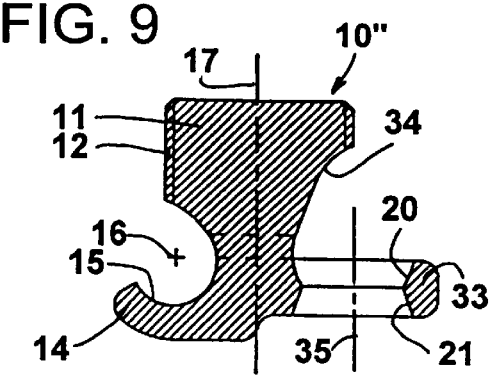
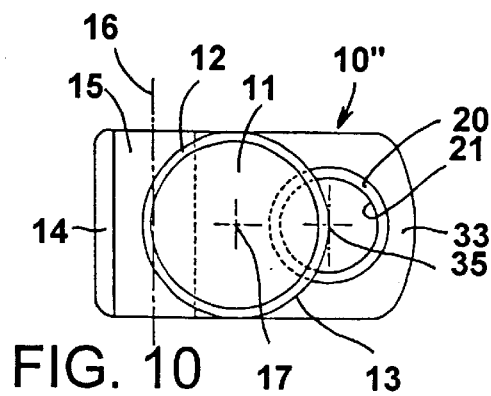
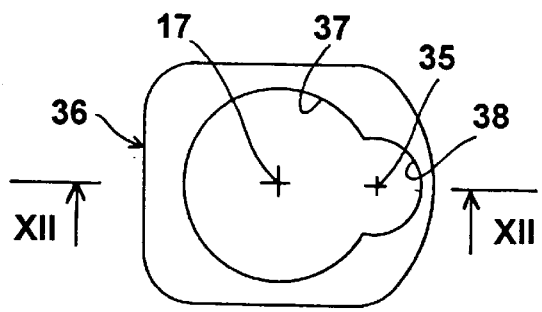
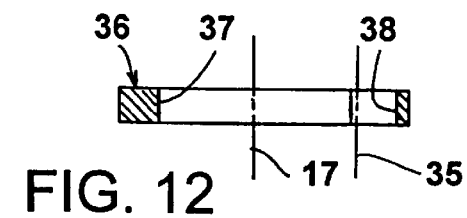

OSTEOSYNTHESIS SYSTEM FOR VERTEBRA ARTHRODESIS

TECHNICAL FIELD

The present invention relates to rachidian osteosynthesis surgery and more precisely to osteosynthesis systems for vertebral arthrodesis, that is to say systems which are intended to immobilize one of at least two adjacent vertebrae with respect to the other.

Among such systems, the invention concerns those which comprise at least one vertebral compression or distraction bar which extends along a part at least of the rachis, at least one and generally at least two vertebral anchoring members, for example a pedicellar screw or a hook, which is for example laminar, thoracic or pedicellar, and, associated with each anchoring member, a common support for receiving, coupling and immobilizing the bar and an end or head of the anchoring member.

In such systems arthrodesis is effected by virtue of locking together the vertebrae in question by the distraction or compression bar which is immobilized with respect to the anchoring members by way of the supports.

Among such systems, the invention concerns those which are of the type referred to as "polyaxial", in which, in opposite relationship to the rachis, the anchoring member has a free end head with a spherical surface in such a fashion that the support and the anchoring member can adopt a relative angular position which can be regulated and modified in all directions, according to the respective needs involved.

Polyaxial systems of that kind are described for example in European patent applications Nos 0 553 042 and 0 613 664. Those systems as illustrated by the two documents referred to hereinbefore by way of example all comprise a hollow support or socket whose open end has a recess or housing for receiving the head of the anchoring member, the cylindrical body of the socket having two longitudinal slots which open into the central bore for the distraction or compression bar to pass transversely with respect to the axis of the socket. To immobilized the assembly, a screwthreaded element is screwed onto the support and directly or indirectly acts on the bar axially with respect to the support, that is to say transversely with respect to the bar, to cause the latter to bear, also directly or indirectly, against the spherical head of the anchoring member, the head thus being pressed firmly against its seat which is disposed in the open end of the support.

Those known polyaxial systems suffer from a major disadvantage which is that the distraction or compression bar can be set in place or removed only by axial displacement with respect to the support, which requires inter alia preliminary removal and in general the absence of the screwthreaded immobilization element.

Another disadvantage of those systems is that it is possible to gain access to the head of the spherical member, in particular by means of a tool, only if the bar and the immobilization means are not there. That is highly inconvenient and troublesome as on the one hand, when setting the anchoring member in place on a vertebra by screwing or hooking, the presence of the bar would be useful in particular for giving the practitioner an indication of the orientation to be imparted to the anchoring member, and on the other hand, once the bar is in place, it is impossible for the practitioner to take action on the anchoring member for adjusting the final position of the arrangement by virtue of the fact that the head of the anchoring member is covered by the bar and, yet again, bearing in mind that the anchoring member has to be fitted into the support prior to its being set in place on the rachis, the support is in no way retained in relation to the anchoring member and therefore has a tendency to float or fall along the shank of the anchoring member, with the result that the operations for setting the anchoring member in position are highly inconvenient and awkward from the point of view of the practitioner.

SUMMARY OF THE INVENTION

The aim of the present invention is in particular to remedy those disadvantages and consequently to provide a system of the foregoing type in which access of the bar to the support and access of the practitioner to the head of the anchoring member are made much more convenient.

For that purpose the system according to the invention comprising at least one vertebral compression or distraction bar capable of extending over a part at least of the rachis, at least one vertebral anchoring member comprising an end head with a spherical surface, an intermediate shank and a vertebral anchoring portion, and, associated with each anchoring member, a common support for receiving, coupling and immobilizing the vertebral anchoring member and the bar, said common support comprising a first concave housing for receiving the bar, a second concave housing for receiving the spherical head, and screwthreaded means for immobilization of the bar and the anchoring member on the support, the immobilization means comprising at least one nut which is screwed onto the screwthreacded portion of the support, is characterised in that the first housing for receiving the bar is disposed to the exterior of the screwthreaded portion of the support and is open laterally and upwardly, in opposite relationship to the rachis, so that the bar is immobilized by a peripheral portion of the nut.

Thus, in the system according to the invention, the operation of setting the distraction or compression bar in position in its housing or the removal thereof therefrom are effected by way of the side and more precisely obliquely by virtue of the fact that the housing for receiving the bar is open to the side and upwardly, which permits in particular those operations when the screwthreaded immobilization element is already or is still partially screwed on the support, with the consequence of affording ease of movement and operation for the practitioner. Moreover the bar does not interfere with the head of the anchoring member.

The first housing for receiving the bar generally has a cylindrical concave surface, the concavity of which is oriented in opposite relationship to the rachis and the axis of which is normal to the axis of the screwthreaded portion of the support. To permit good co-operation of the nut with the bar, the surface which defines the first housing preferably intersects the cylindrical surface of the screwthreaded portion of the support so that the nut comes to bear against the bar, directly or indirectly, substantially in line with the axis of the bar.

As regards the concave surface of the second housing for receiving the spherical head of the anchoring member, it is advantageously also spherical, although it may also be conical. The concavity of that second housing is also oriented in opposite relationship to the rachis.

Advantageously, the nut may have teeth on its radial face for clamping the bar, such teeth being of a nature as to increase the amount of friction and thus avoid untimely slackening of the nut.

To permit relative angular regulation of the support and the anchoring member, the second housing for receiving the spherical head of the anchoring member is prolonged towards the rachis by an opening for the intermediate shank of the anchoring member to pass therethrough, the passage opening being of a larger diameter than the diameter of the intermediate shank. Preferably that opening flares towards the rachis and it is for example conical.

Preferably the screwthreaded means for immobilization of the bar and the head of the anchoring member are so arranged as to afford access from the exterior to an operating profile of the head, for example a polygonal recess, when they are in place on the support. In general the screwthreaded means will have an axial opening permitting the passage of a tool.

In accordance with a first embodiment the second housing for receiving the spherical head of the anchoring member constitutes the bottom of the portion of the support, which is hollow and open axially therethrough.

In this embodiment preferably the two housings communicate laterally through the wall of the support so that the bar and the spherical head bear against each other upon immobilization thereof; in other words, the distance between the centers of the two housings is preferably equal to and indeed substantially less than the sum of the radii of the bar and the head of the anchoring member. Preferably the two housings are so arranged that upon assembly the axis of the bar and the center of the spherical head are in a transverse plane perpendicular to the axis of the hollow portion of the support.

In accordance with a first configuration of this first embodiment., there is provided a screw, preferably without a head and of countersink type, capable of co-operating with an internal thread of the hollow support and having a hollow operating recess which is for example hexagonal, to permit immobilization of the spherical head of the anchoring member in its housing, that is to say with respect to the support.

Advantageously, the screw is hollow therethrough to permit access through it for a tool involving the operating profile of the head of the anchoring member.

As regards the nut, it can co-operate with the bar either directly or indirectly by means of an intermediate part forming a washer.

In accordance with a second configuration of this first embodiment, there is provided an intermediate part which is formed by a central portion for bearing against the head of the anchoring member and which is intended to be received in the smooth bore of the hollow support, and two arms passing through the wall of the hollow support by way of two longitudinal slots therein, and which are preferably in opposite and aligned relationship, one of the free ends of the arms, which are external to the hollow support, being intended to come to bear against the bar, the assembly being such that the nut bears against the free ends of the two arms, urging the intermediate part simultaneously against the head of the anchoring member by way of its central portion and against the bar by way of the free end of one of its two arms.

Advantageously the central portion of the intermediate part has an opening for access to the operating profile of the head of the anchoring member for a tool.

Moreover the intermediate part is arranged to bear by way of a face simultaneously against the bar and against the head of the anchoring member, so as to permit correct immobilization of those two elements by the nut.

In accordance with a second embodiment of the invention, the second housing for receiving the anchoring member is also disposed to the exterior of the screwthreaded portion of the support which is preferably solid in its screwthreaded portion, and the second housing is open laterally and upwardly, in opposite relationship to the rachis, so that the spherical head of the anchoring member is also locked by the nut. In that case, the nut immobilizes the bar and the head of the anchoring member to the exterior of the support, by the peripheral portion thereof, either by an indirect action or preferably by way of a washer.

The washer has a central opening by way of which it is fitted onto the screwthreaded portion of the support and which is prolonged laterally by a window, for example of an arcuate shape, which affords access to the operating profile of the head of the anchoring member for a tool.

In this second embodiment to achieve good distribution of the forces and good immobilization, the two housings are preferably in diametrally opposite relationship with respect to the support and to the nut.

In all the embodiments of the invention, the nut may advantageously have, on its radial face which is in opposite relationship to the rachis, operating recesses intended to co-operate with a tightening tool of the pin-wrench type.

BRIEF DESCRIPTION OF THE DRAWINGS

The invention will be more clearly appreciated from the following description with reference to the accompanying drawings which are part of the description and in which:

FIG. 1 is a partly sectional. broken-away exploded elevational view of a system in accordance with a first embodiment of the invention, in its use with a pedicellar screw, FIG. 2 is a partly sectional elevational view of the system of FIG. 1 in the assembled state, FIG. 3 is an axial plan view of the support of the system of FIGS. 1 and 2, FIG. 4 is a view similar to FIG. 2 relating to the use of an anchoring member which is in the form of a hook, FIG. 5 is a view similar to FIGS. 2 and 4 relating to an alternative embodiment of the means for immobilization of the bar and the anchoring member with respect to the support, only part of the anchoring member being shown here, FIG. 6 is an axial plan view of the support of the system of FIG. 5, FIG. 7 is an axial plan view of the intermediate part of FIG. 5, which is disposed between on the one hand the nut and on the other hand the bar and the head of the anchoring member, FIG. 8 is a view similar to FIGS. 2, 4 and 5 relating to a second embodiment of the system according to the invention, illustrated here in its use with a pedicellar screw, FIG. 9 is a view in axial section showing the support of the system of FIG. 8, FIG. 10 is an axial plan view of the support of FIG. 9, FIG. 11 is an axial plan view of the intermediate part of the system of FIG. 8, this part being of the washer type and being disposed between on the one hand the tightening nut and on the other hand the bar and the head of the anchoring member, and FIG. 12 is a view in axial section taken along line XII—XII of the intermediate part shown in FIG. 11.

DETAILED DESCRIPTION OF THE INVENTION

In all the embodiments of the invention which will be described hereinafter by way of example, the osteosynthesis system for vertebral arthrodesis comprises a vertebral compression or distraction bar 1 which IS smooth or which has roughness portions and which extends along a part at least of the rachis. At spaced locations the bar 1 is received and immobilized by supports which each receive and immobilize a vertebral anchoring member of the polyaxial type, for example a pedicellar screw 2 or a hook 3, which is for example laminar, thoracic or pedicellar. The anchoring member 2, 3 comprises, for co-operation thereof with the support, an end head 4 having a spherical surface 5, an intermediate shank 6 following the head and a vertebral anchoring portion in the narrow sense, which is formed either by a screwthreaded shank 7 in the case of a pedicellar screw or by a terminal portion 8 of a hook configuration, in the case of a hook.

As described hereinafter, the bar 1 and the head 4 are received by the support and are coupled and immobilized thereto by screwthreaded means which comprise at least one nut 9.

Reference will firstly be made to FIGS. 1 to 4 to describe a first embodiment of the system according to the invention in terms of its use with a pedicellar screw (FIGS. 1 to 3) and with a hook (FIG. 4).

The support 10 of FIGS. 1 to 4 is formed by a body in one pierce which has a main cylindrical portion 11 provided over its entire length, from its end opposite to the rachis, that is to say from its upper end in FIGS. 1, 2 and 4, with a male screwthread 12. The main cylindrical portion 11 is prolonged towards the rachis by a smooth cylindrical portion 13 which has a lateral protuberance or projecting portion 14 which in axial projection extends considerably beyond the circular contour of the main portion 11.

Provided in the protuberance 14 is a cylindrical concave recess or housing 15, the concavity of which is oriented in opposite relationship to the rachis and is of a diameter substantially equal to that of the bar 1 and preferably very slightly less than same in order to provide for better face co-operation between the bar and its housing. As can be seen from FIGS. 1, 2 and 4 the cylindrical housing 15 is therefore disposed in part to the exterior of the main cylindrical portion 11 of the support 10 and it is open or issues laterally and upwardly, that is to say obliquely, to the exterior, in opposite relationship to the rachis, which permits the bar 1 to be set in position and removed by way of the side. The axis 16 of the cylindrical housing 15 is normal to the axis 17 of the cylindrical portion 11 and it is disposed at a spacing therefrom such that, as shown in FIGS. 2 and 4, the nut 9 bears against the bar 1 radially, that is to say along a generatrix in vertical alignment with the common axis 16 of the bar and the housing 15 when the bar is in place.

In the illustrated example the nut 9 bears directly against the bar 1 by way of its lower radial surface which preferably, as shown in FIG. 1, has teeth 18 for increasing the amount of friction and of such a nature as to prevent untimely slackening of the nut. In an alternative configuration, it would be possible to provide an intermediate washer between the nut and the bar.

In this embodiment the support 10 is hollow therethrough and it successively has in coaxial relationship, from its end in opposite relationship to the protuberance 14, a screwthreaded cylindrical bore 19, a concave recess or housing 20 for the spherical head 4 of the anchoring member, and a terminal opening 21 for the intermediate shank 6 of the anchoring member to pass therethrough.

The diameter of the screwthreaded bore 19 is equal to or substantially greater than that of the head 4 of the anchoring member to permit introduction of the head while the housing 20 forms a concave constriction to constitute a seat. The housing 20 whose concavity is oriented in opposite relationship to the rachis may be conical or preferably, as shown, in the form of a portion of a sphere whose radius is equal to that of the spherical head 4 so as to provide a pivot connection of the ball joint type. The terminal opening 21 flares downwardly, that is to say towards the rachis, for example in a conical configuration, from the end of the housing 20 opposite to the screwthreaded bore 19, to permit angular adjustment of the relative position between the support 19 and the anchoring member 2, 3. At its junction to the housing 20, the opening 21, for the same purpose and as shown in FIGS. 2 and 4 is of a diameter which is larger than that of the intermediate shank 6 of the anchoring member.

In accordance with an advantageous feature which can also be seen from the drawings the housings 15 and 20 communicate laterally with each other through the wall of the support 10 so that, when the arrangement is tightened, the bar 1 and the spherical head 4 of the anchoring member bear against each other, which increases the immobilization effect for the assembly. For that purpose, the shortest distance between the axes 16 and 17 is equal to or preferably slightly less than the sum of the radii of the bar 1 and the head 4. Moreover, the housings 15, 20 are so arranged that, upon assembly, the common axis 16 of the bar 1 and the center of the head 4 are at the same height, that is to say in a transverse plane perpendicular to the axis 17 of the support 10.

For tightening it in the vertebral body, the spherical head 4 of the anchoring member 2, 3 has a hollow recess 22, for example polygonal and in particular hexagonal, being intended to receive a male tool of complementary profile.

To immobilize the head 4 with respect to the support 10, the arrangement has a screw 23 intended to co-operate with the screwthreaded bore 19 in the support 10 and having a hollow recess 23 which is for example also polygonal and in particular hexagonal, for receiving a male tool of complementary profile. In accordance with an advantageous feature, the screw 23 is hollow therethrough to permit access for the first tool to the recess 22 in the head 4 and thus to permit external manual actior on the anchoring member when the locking screw 23 is already in place. For that purpose the recess 24 is larger than the recess 22 and it is preferably prolonged by a cylindrical bore 25 of a diameter that is at least equal to the diameter of the circumscribed circle of the recess 22, also defining a shoulder 26 acting as an axial abutment for the tool for operating the screw 23. As can be seen from the drawings, the screw 23 is without a head, which permits it to be totally countersunk in the support 10 when the arrangement is tightened (FIGS. 2 and 4). Upon tightening, it bears against the head 4 along the lower circular edge of the bore 25.

For operation of the nut 9, the nut 9, on its radial face which is opposite to the teeth 18, may comprise recesses 27 for co-operating with a complementary pin-type tool.

In the embodiment shown in FIGS. 1 to 4 which has just been described hereinbefore, the screwthreaded means for immobilization of the bar 1 and the anchoring member 2, 3 on the support 10 are formed by two separate elements which are operated independently, namely the nut 9 for the bar 1 and the screw 23 for the anchoring member.

When the anchoring member 2, 3 is carried by the support 10, the screw 23 can be screwed but without clamping the head 4 so that there is a slight clearance between the support and the head, which permits the anchoring member to be set in place on the rachis by acting through the screw 23, without the support 10 floating or falling along the intermediate shank 6. In that operation of setting the anchoring member in position, the nut 9 may be present on its screwthread 12, without causing any problem or inconvenience, and the bar 1 may also be present in its housing 15, without the nut 9 being completely tightened; that enables the practitioner, before final locking by means of the nut 9 and the screw 23, to finely adjust the relative positions of the anchoring member 2, 3, the support 10 and the bar 1.

In addition, after that final locking operation, the practitioner can also independently and selectively adjust the relative position of the support 10 and the bar 1 and/or the head 4 by slightly loosening the nut 9 and/or the screw 23 respectively, followed by adjustment to the desired position and re-tightening.

Reference will now be made to FIGS. 5 to 7 to describe an alternative configuration of the embodiment of FIGS. 1 to 4, in which respect it will be appreciated that this alternative configuration can indeed be applied to a use both with the pedicellar screw 2 and with tthle hook 3.

This alternative configuration is essentially characterised in that immobilization of the bar 1 and the spherical head 4 of the anchoring member 2, 3 is effected solely by the nut 9, by means of an intermediate part 28 which co-operates on the one hand with the nut 9 and on the other hand with the bar 1 and the spherical head 4.

In its lower portion for receiving the bar 1 and the spherical head 4 the support 10' is identical or similar to the support 10. On this subject therefore reference may be made to the description which was set forth in relation to the support 10. In its upper portion the support 10' also comprises a main cylindrical portion 11 which is screwthreaded at 12 to receive the nut 9 which is also identical to that of FIGS. 1 to 4.

The support 10' is also hollow therethrough and, in its upper portion, that is to say above the housing 20, it has a smooth cylindrical bore 19' for the passage of the spherical head 4 and, as described hereinafter, the central portion of the intermediate part 28.

The intermediate part 28, comprises a central portion 29 and two arms 30 protecting outwardly from the central portion 29 and which are preferably in opposite and aligned relationship. The central portion 29 is circular, with an outside diameter that is equal to or scarcely less than the diameter of the cylindrical bore 19', and it has a central circular opening 31 permitting access of the tightening tool to the operating recess in the spherical head 4. The radial arms 30 of the intermediate part 28 pass through the wall of the cylindrical portion 11 of the support 10' by way of two longitudinal slots 32 which extend axially over a distance such that the intermediate part 28 can come to bear by way of its central portion 29 against the spherical head 4 and by way of the end of one of its arms 30 against the bar 1, in vertical alignment with the axis 16 of the housing 15. Consequently, from the central portion 29 the arms 30 pans through the wall of the support 10' so that their free ends are disposed on the outside of the support in such a way as to co-operate by way of one face with the nut 9 and by way of the other face, in regard to only one of the arms 30, with the bar 1.

When the arrangement is tightened, the nut 9 bears against the diametrally opposite free ends of the arms 30, which urges the central portion 29 against the spherical head of the anchoring member, by way of the circular lower edge of the opening 31, on the outside of the recess in the head 4, and the free end of one of the arms 30 against the bar.

In this embodiment the longitudinal slot 32 which is disposed on the side of the housing 15 can be totally open in its lower portion, to open into the housing 15 for the bar 1. As shown in FIG. 6 the axial plane of the slots 32 is perpendicular to the axis 16 of the bar housing 15.

When the anchoring member 2, 3 is set in place on the rachis, the nut 9 and the intermediate part 28 are preferably already present on the support 10', but without clamping of the head 4 to permit a slight play between the head and the support. That prevents the support from excessively floating or from dropping down along the intermediate shank. In addition the bar 1 can also be present in its housing 15, without involving a clamping effect and without interfering with the action of the practitioner on the head 4. In contrast, the simultaneous presence of the bar 1, the support 10' and the anchoring member 2, 3 permits the practitioner to finely adjust the relative position of those elements, before final locking by means of the nut 9.

Reference will now be made to FIGS. 8 to 12 to describe the second embodiment of the system according to the invention.

This second embodiment essentially differs from the preceding embodiment in that, as described hereinafter, the housing for receiving the spherical head of the anchoring member is also disposed on the exterior of the screwthreaded portion of the support and is open laterally and upwardly so that the spherical head of the anchoring member is also locked by the nut and the second housing is accessible from the side and no longer axially by way of the interior of the body of the support.

As before, in its lower portion, the support 10" comprises the protuberance 14 defining the housing 15 for receiving the bar 1, the geometrical arrangement of the housing 15 being the same as previously so that reference may be made to the foregoing description.

In this embodiment, the main cylindrical portion 11 of the support 10" is solid, that is to say it does not have a bore, and, as previously, it externally comprises the screwthread 12 for receiving the nut 9 which is also identical or similar to the nut 9 which has been described hereinbefore.

In its lower portion, and in opposite relationship to the protuberance 14, the body of the support 10" comprises a lateral protuberance or projecting portion 33 above which is disposed a wide recess 34 which is disposed over the cylindrical portion 11 of the body of the support 10" and which reduces in depth in an upward direction. The protuberance 33 is hollow therethrough and its bore is formed by a housing 20 and by a passage opening 21 which are identical to those which have beer described hereinbefore respectively for receiving the cylindrical head 4 of the anchoring member shown here by way of example by means of the pedicellar screw 2 and for the passage of the intermediate shank 6 of that member. The axis 35 of the bore 20, 21 is parallel to the axis 17 of the main cylindrical portion 11 of the support and it is preferably disposed substantially at the same spacing therefrom as the axis 16 of the housing 15 for the bar 1. Because the protuberances 14 and 33 are in opposite relationship, the plane of the axes 17 and 35 is perpendicular to the axis 16 of the bar housing 15.

Clamping of the bar 1 and spherical head 4 by the nut 9 is implemented by means of an intermediate part 36 of the washer type. The washer 36 has a central circular opening 37 for the cylindrical portion 11 of the support to pass therethrough, the opening 37 being prolonged on the side of the bore 20, 21 by an arcuate window 38 which is coaxial with the bore 20, 21 so that, as shown in FIG. 8, its lower arcuate edge comes to co-operate with the spherical head of the anchoring member when the arrangement is tightened, to the exterior of the recess 22. Moreover the window 38 permits access for the tool to the head of the anchoring member, in particular in the case of a pedicellar screw. The recess 34 permits the passage of the anchoring member and the tool for operating same.

When the nut 9 is tightened, the washer 36 comes to bear along two diametrally opposite zones respectively against the bar 1 and the spherical head 4 of the anchoring member, thereby ensuring good distribution of the forces and an excellent locking action.

In this embodiment the nut 9 cannot be present on the support 10" when the anchoring member is set in place on the rachis, because the recess 22 is in vertical alignment with the screwthread 12. The support 10" is therefore not retained.

On the other hand, this embodiment has the same advantage linked to the possibility of having access to the anchoring member when the bar 1 is set in place, but with the need to remove the nut 9.

In the various embodiments of the invention the spherical head 4, in the case of the pedicellar screw 2, is of a diameter that is generally greater than that of the intermediate shank 6 and the screwthreaded shark 7, so that the pedicellar screw can be produced in one piece and can be fitted into the support 10, 10' or 10". On the other hand, if the diameter of the spherical head 4 is smaller than one or other of the diameters of the intermediate shank 6 and the screwthreaded shank 7, such an axial fitting operation is not possible, and in that case, the pedicellar screw will be manufactured in two parts which will be fitted together after the spherical head 9 has been set in place in its housing 20. This also applies to the situation in which the anchoring member is formed by the hook 3 shown in FIG. 4 which can be used in all the embodiments of the invention. In this case the free end of the intermediate shank 6 carries a male screwthread 39 co-operating with a screwthread 40 in the hook-shaped portion 8.

It will be appreciated that the invention is not limited to the embodiments which have been described above; on the contrary it would be possible to envisage various alternative configurations without thereby departing from the scope of the invention.

What is claimed is:

1. An osteosynthesis system for vertebral arthrodesis, comprising: at least one vertebral compression or distraction bar capable of extending over a portion at least of a rachis; at least one orientable vertebral anchoring member comprising a head having a spherical surface and a vertebral anchoring portion;

a common support for receiving, coupling and immobilizing said vertebral anchoring member and said bar, said common support comprising a first concave housing for receiving the bar, said first concave housing being open laterally and upwardly in opposite relationship to said anchoring portion, and a second concave housing for receiving said head, said second concave housing being so arranged that the head can occupy with respect to the support any regulatable angular position about a center of said second concave housing, the first concave housing, being laterally offset with respect to said second concave housing; and screwthreaded means for immobilization of the bar and the anchoring member on the support, said screwthreaded means comprising at least one nut which is screwed onto a screwthreaded portion, wherein said screwthreaded portion belongs to the support; at least a portion of the first concave housing is disposed laterally to an exterior of said screwthreaded portion; the head of the anchoring member constitutes an end of the anchoring member which is opposite to the anchoring portion; and the concavity of the first and second concave housings is directed axially in opposite relationship to the anchoring portion of the anchoring member, the assembly being such that when the nut is screwed onto the screwthreaded portion of the support, the nut axially immobilizes the bar in said first concave housing.

2. A system according to claim 1 wherein the first concave housing has a cylindrical concave surface whose concavity is oriented in opposite relationship to the rachis and of which the axis is normal to an axis of the screwthreaded portion of the support.

3. A system according to claim 1 wherein a surface defining the first concave housing intersects a cylindrical surface of the screwthreaded portion of the support.

4. A system according to claim 1 wherein a concave surface of the second concave housing is spherical or conical and the concavity of that surface is oriented in opposite relationship to the rachis.

5. A system according to claim 1 wherein the nut has teeth on a radial surface thereof for clamping the bar.

6. A system according to claim 1 wherein the second concave housing is extended towards the rachis by an opening for passage of an intermediate shank of the anchoring member, said shank being disposed between the head and the anchoring portion of the anchoring member.

7. A system according to claim 6 wherein the opening for the passage of the intermediate shank is of a diameter which is larger than a diameter of said intermediate shank to permit adjustment of the angular position of the anchoring member with respect to the support in all directions.

8. A system according to claim 7 wherein the opening flares toward the rachis and is conical.

9. A system according to claim 1 wherein the second concave housing constitutes a bottom of the screwthreaded portion of the support.

10. A system according to claim 9 wherein the first and second concave housings communicate laterally with each other through a wall of the support so that the bar and the head bear against each other upon immobilization thereof, a spacing between axes of the two concave housings being equal or slightly less than a sum of radii of the bar and the head.

11. A system according to claim 9 further comprising a screw cooperative with a female screwthread of the support and having ahollow operating recess which is polygonal to permit immobilization for the head of the anchoring member in the second concave housing.

12. A system according to claim 11 wherein the screw is hollow therethrough to permit access for a tool to an operating profile provided in the head of the anchoring member.

13. A system according to claim 9 further comprising an intermediate part formed by a central portion for bearing against the head of the anchoring member and received in a smooth bore of the support and two arms passing through a wall of the support by way of two longitudinal slots therein which are opposite and aligned, one free end of the arms which are external to the support bearing against the bar, the assembly being such that the nut bears against free ends of the two arms urging the intermediate part simultaneously against the head of the anchoring member by way of central portion and against the bar by way of the free end of one of two arms.

14. A system according to claim 13 wherein the central portion of the intermediate part has an opening, an edge thereof bearing along a circular configuration against the head of the anchoring member and which permits access for a tool to an operating profile provided in said head.

15. A system according to claim 1 wherein the nut co-operates directly with the bar.

16. A system according to claim 1 wherein the second concave housing is disposed to an exterior of the screwthreaded portion of the support, the head of the anchoring member being blocked by the nut on an outside of the support.

17. A system according to claim 16 wherein the nut acts on the bar and on the head by way of a washer.

18. A system according to claim 16 wherein the first and second concave housings are in diametrically opposite relationship with respect to the support and the nut.

19. A system according to claim 17 wherein the washer has a window, an edge of said window being cooperative along a circular arc with the head and which permits access for a tool to an operating profile carried by the head.

20. A system according to claim 1 wherein a radial face of said nut in opposite relationship to the rachis has operating recessses cooperative with a tightening tool.

21. A system according to claim 1 wherein the anchoring member is formed by pedicellar screws and hooks.

22. A system according to claim 1 wherein the screwthreaded means for immobilization of the bar and the head of the anchoring member are arranged to afford access from an exterior thereof to an operating profile carried by said head.

* * * * *